United States Patent
Sako et al.

(10) Patent No.: US 6,709,648 B2
(45) Date of Patent: Mar. 23, 2004

(54) HAIR CONDITIONING COMPOSITION COMPRISING SILICONES AND FRIZZ CONTROL AGENTS

(75) Inventors: Takashi Sako, Higashinada-ku (JP); Arata Mitsumatsu, Nishinomiya (JP); Yoshinari Okuyama, Higashinada-ku (JP); Mikio Uchida, Ashiya (JP); James Albert Monton, Cincinnati, OH (US); Luisa Navarro Cerda, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/303,615

(22) Filed: Nov. 25, 2002

(65) Prior Publication Data

US 2003/0108504 A1 Jun. 12, 2003

Related U.S. Application Data

(63) Continuation of application No. PCT/US01/17077, filed on May 29, 2001.

(30) Foreign Application Priority Data

May 30, 2000 (WO) .................. PCT/US00/14869
Nov. 3, 2000 (WO) .................. PCT/US00/30342

(51) Int. Cl.[7] .................................. A61K 7/08
(52) U.S. Cl. .................. 424/70.12; 424/70.15
(58) Field of Search .................. 424/70.12, 70.15

(56) References Cited

U.S. PATENT DOCUMENTS 5,482,703 A * 1/1996 Pings ...................... 424/70.12
5,490,982 A    2/1996 Siciliano
5,531,986 A    7/1996 Shevade et al.
5,567,428 A * 10/1996 Hughes ...................... 424/401
5,612,301 A *  3/1997 Inman ...................... 510/122
5,753,216 A    5/1998 Leitch et al.
5,989,532 A   11/1999 Haning et al.
6,149,898 A * 11/2000 Peffly et al. ............. 424/70.12

FOREIGN PATENT DOCUMENTS

EP          0861655 A2      9/1998
WO          WO-92/17154 A1  10/1992

* cited by examiner

Primary Examiner—Jyothsna Venkat
(74) Attorney, Agent, or Firm—Linda M. Sivik; Brian M. Bolam

(57) ABSTRACT

Disclosed is a hair conditioning composition comprising:

(1) a non-volatile silicone compound which has a molecular weight of from about 100,000 to about 1,500,000 and has a viscosity of from about 500,000 to about 50,000,000 mpa·s;

(2) a volatile compound selected from the group consisting of an isoparaffin hydrocarbon having a boiling point of from about 60 to about 260° C., a volatile silicone compound having from 2 to 7 silicon atoms, and mixtures thereof; and (3) a frizz control agent selected from the group consisting of (i), (ii), and (iii):
   (i) PEG-modified glycerides;
   (ii) PEG-modified glyceryl fatty acid esters; and
   (iii) mixtures thereof.

16 Claims, No Drawings

HAIR CONDITIONING COMPOSITION COMPRISING SILICONES AND FRIZZ CONTROL AGENTS

CROSS REFERENCE TO RELATED APPLICATION

The application is a continuation of International application PCT/US01/17077 (Case AA-475M2) filed on May 29, 2001, which claims priority to International application PCT/US00/30342 (Case AA-475M) filed on Nov. 3, 2000, and PCT/US00/14869 (Case AA475F) filed on May 30, 2000.

TECHNICAL FIELD

The present invention relates to hair conditioning compositions comprising silicone compounds and frizz control agents.

BACKGROUND

Hair is often subjected to a wide variety of insults that can cause damage. These include shampooing, rinsing, drying, heating, combing, styling, perming, coloring, exposure to the elements, etc. Thus, the hair is often in a dry, rough, lusterless or frizzy condition due to abrasion of the hair surface and removal of the hair's natural oils and other natural conditioning and moisturizing components. Additionally, hair is subjected to weather-related changes, such as changes in humidity, which can leave hair in a frizzy condition.

Frizzy condition of the hair often causes an expanded and unruly hair and makes it difficult to control the hair style. For consumers who desire well aligned hair, such expanded and unruly hair is not desirable. The term "frizz control" herein means to control hair frizz, i.e., to reduce frizz condition of the hair or to prevent the hair from causing frizzy condition.

A variety of approaches have been developed to control hair frizz. These include reactive chemistry approaches aimed at a permanent restructuring of hair, and application of oily leave-on products to weigh down hair. The use of reactive chemistry provides a permanent frizz reduction benefit. However, the reactive chemistry methods and compositions are harsh on the hair structure and can cause hair to split or break and can also result in a loss of hair shine. Skin and/or eye irritation from the relatively harsh chemicals used in reactive chemistry methods is also common.

Typically, leave-on conditioner type hair formulations provide advantages over other more permanent frizz reduction approaches. For example, leave-on formulations are typically less damaging to the hair. Also, leave-on formulations are more convenient because the consumer can use the product at any time and then wash the product out of the hair with one washing. Another benefit is that the product may be applied to parts of the hair most in need of the frizz control benefits.

Commonly, hair conditioning benefits are provided through the use of hair conditioning agents such as cationic surfactants, cationic polymers, silicone conditioning agents, hydrocarbon and other organic oils and solid aliphatics such as fatty alcohols. However, such conditioning agents are often impractical for using in the large amounts necessary to control hair frizz. Usage of large amounts of conditioning agents that work to control hair frizz by coating and weighing down the hair commonly results in a poor perception of hair cleanliness and hair feel, for example, leaving the hair and hands with a tacky, dirty, feeling.

Based on the foregoing, there remains a desire to provide hair conditioning compositions which provide improved frizz control benefit while retaining good conditioning benefits and good hair feel and appearance, i.e., which provide improved frizz control benefit in addition to other conditioning benefits such as smoothness, softness, and reduction of friction, while reducing sticky and greasy feeling.

None of the existing art provides all of the advantages and benefits of the present invention.

SUMMARY

The present invention is directed to a hair conditioning composition comprising:

(1) a non-volatile silicone compound which has a molecular weight of from about 100,000 to about 1,500,000 and has a viscosity of from about 500,000 to about 50,000,000 mPa·s;

(2) a volatile compound selected from the group consisting of an isoparaffin hydrocarbon having a boiling point of from about 60 to about 260° C., a volatile silicone compound having from 2 to 7 silicon atoms, and mixtures thereof; and (3) a frizz control agent selected from the group consisting of (i), (ii), and (iii):

(i) PEG-modified glycerides having the structure:

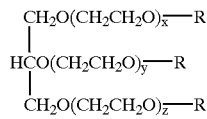

wherein one or more of the R groups is selected from saturated or unsaturated fatty acid moieties derived from animal or vegetable oils wherein the fatty acid moieties have a carbon length chain of from 12 and 22, any other R groups are hydrogen, x, y, z are independently zero or more, the average sum of x+y+z is equal to from about 10 to about 45;

(ii) PEG-modified glyceryl fatty acid esters having the structure:

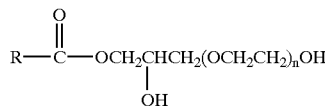

wherein R is an aliphatic group having from 12 to 22 carbon chain length, and n has an average value of from 5 to 40;

(iii) mixtures thereof.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

All cited references are incorporated herein by reference in their entireties. Citation of any reference is not an admission regarding any determination as to its availability as prior art to the claimed invention.

Herein, "comprising" means that other steps and other ingredients which do not affect the end result can be added.

This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

The aspects and embodiments of the present invention set forth in this document have many advantages. For example, the hair conditioning compositions of the present invention provide improved conditioning benefits to the hair, especially, provide improved frizz control benefit in addition to other conditioning benefits such as smoothness, softness, and reduction of friction, and leave the hair and hands with a clean feeling.

Non-Volatile Silicone Compound

The compositions of the present invention comprise a non-volatile silicone compound.

The non-volatile silicone compound of the present invention has a molecular weight of from about 100,000 to about 1,500,000, more preferably from about 100,000 to about 1,000,000, and even more preferably from about 120,000 to about 600,000.

The non-volatile silicone compound of the present invention has a viscosity of from about 500,000 to about 50,000,000 mPa·s at 25° C., more preferably from about 600,000 to about 30,000,000 mPa·s, and even more preferably from about 800,000 to about 10,000,000 mPa·s. The viscosity can be measured by means of a glass capillary viscometer as set forth in Dow Corning Corporate Test Method CTM0004, Jul. 20, 1970.

The non-volatile silicone compound useful herein is believed to provide conditioning benefits to the hair such as smoothness, softness, and combing ease.

The non-volatile silicone compound can be included in the composition of the present invention at a level by weight of preferably from about 0.5% to about 30%. Especially, in a non-aqueous composition of the present invention, the non-volatile silicone compound can be included at a level by weight of preferably from about 1% to about 30%, more preferably from about 3% to about 25%, still preferably from about 5% to about 20%. Especially, in an aqueous composition of the present invention, the non-volatile silicone compound can be included at a level by weight of preferably from about 0.5% to about 20%, more preferably from about 0.75% to about 15%, still preferably from about 1% to about 15%.

Silicone compound of high molecular weight may be made by emulsion polymerization. The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof A nonvolatile dispersed silicone that can be especially useful is a silicone gum. The term "silicone gum", as used herein, means a polyorganosiloxane material having a viscosity at 25° C. of greater than or equal to 1,000,000 mPa·s. It is recognized that the silicone gums described herein can also have some overlap with the below-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof.

Also useful are silicone resins, which are highly crosslinked polymeric siloxane systems. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

The method of manufacturing these silicone compounds, can be found in Encyclopedia of Polymer Science and Engineering, Volume 15, Second Edition, pp. 204–308, John Wiley & Sons, Inc., 1989.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The silicone compounds useful herein include polyalkyl or polyaryl siloxanes with the following structure (I)

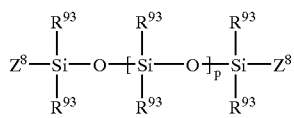
(I)

wherein $R^{93}$ is alkyl or aryl, and x is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

Other silicone compounds include amino substituted materials. Suitable alkylamino substituted silicone compounds include those represented by the following structure (II)

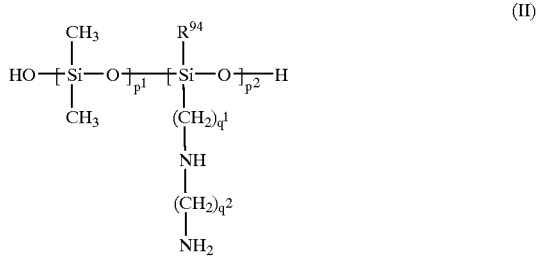
(II)

wherein $R^{94}$ is H, $CH_3$ or OH, $p^1$, $p^2$, $q^1$ and $q^2$ are integers which depend on the molecular weight, the average molecular weight being approximately between 5,000 and 10,000. This polymer is also known as "amodimethicone".

Suitable amino substituted silicone fluids include those represented by the formula (III)

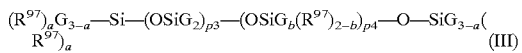
(III)

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum $p^3+p^4$ is a number from 1 to 2,000 and preferably from 50 to 150, $p^3$ being able to denote a number from 0 to 1,999 and preferably from 49 to 149 and $p^4$ being able to denote an integer from 1 to 2,000 and preferably from 1 to 10; $R^{97}$ is a monovalent radical of formula $C_{q3}H_{2q3}L$ in which $q^3$ is an integer from 2 to 8 and L is chosen from the groups

—N($R^{96}$)$CH_2$—$CH_2$—N($R^{96}$)$_2$

—N($R^{96}$)$_2$

—N($R^{96}$)$_3$X'

—N($R^{96}$)$CH_2$—$CH_2$—NR$^{96}$H$_2$X' in which $R^{96}$ is chosen from the group consisting of hydrogen, phenyl, benzyl, a saturated hydrocarbon radical, preferably an alkyl radical containing from 1 to 20 carbon atoms, and X' denotes a halide ion.

An especially preferred amino substituted silicone corresponding to formula (II) is the polymer known as "trimethylsilylamodimethicone" wherein $R^{94}$ is $CH_3$.

Other amino substituted silicone polymers which can be used are represented by the formula (V):

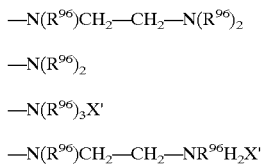

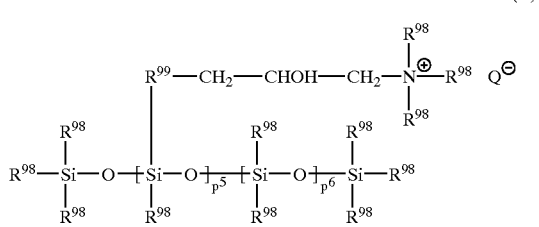
(V)

where $R^{98}$ denotes a monovalent hydrocarbon radical having from 1 to 18 carbon atoms, preferably an alkyl or alkenyl radical such as methyl; $R^{99}$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; $p^5$ denotes an average statistical value from 2 to 20, preferably from 2 to 8; $p^6$ denotes an average statistical value from 20 to 200, and preferably from 20 to 50. A preferred polymer of this class is available from Union Carbide under the name "UCAR SILICONE ALE 56."

References disclosing suitable nonvolatile dispersed silicone compounds include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston. "Silicon Compounds" distributed by Petrarch Systems, Inc., 1984, provides an extensive, though not exclusive, listing of suitable silicone compounds.

Particularly suitable silicone compounds herein are nonvolatile silicone oils having a molecular weight of from about 200,000 to about 600,000 such as Dimethicone, and Dimethiconol. These silicone compounds can be incorporated in the composition as silicone oils solutions; the silicone oils being volatile or non-volatile.

Commercially available silicone compounds which are useful herein include Dimethicone gum solutions with tradenames SE 30, SE 33, SE 54 and SE 76 available from General Electric, Dimethiconol with tradename DCQ2-1401 available from Dow Corning Corporation, Mixture of Dimethicone and Dimethiconol with tradename DC1403 available from Dow Corning Corporation, and emulsion polymerized Dimethiconol available from Toshiba Silicone as described in GB application 2,303,857.

Volatile Compound

The compositions of the present invention comprise a volatile compound selected from the group consisting of an isoparaffin hydrocarbon having a boiling point of from about 60 to about 260° C., a volatile silicone compound having from 2 to 7 silicon atoms, and mixtures thereof. The volatile silicone is preferably used in the present compositions of the present invention, and more preferably, a volatile cyclic silicone compound is used in the compositions of the present invention. The volatile compound useful herein is believed to reduce sticky and greasy feeling, and leave the hair and hands with a clean feeling.

The volatile compound can be selected according to the compatibility with other components, and other desired characteristic of the composition of the present invention, for example, can be included in the composition of the present invention at a level by weight of preferably from about 5% to about 98.9%. Especially, in a non-aqueous composition of the present invention, the volatile compound can be included at a level by weight of preferably from about 50% to about 98.9%, more preferably from about 55% to about 98%, still preferably from about 60% to about 95%. Especially, in an aqueous composition of the present invention, the volatile compound can be included at a level by weight of preferably from about 5% to about 70%, more preferably from about 10% to about 65%, still preferably from about 20% to about 50%.

The volatile isoparaffin hydrocarbons useful herein have a boiling point of from about 60 to about 260° C. Commercially available volatile isoparaffin hydrocarbons useful herein include Isopar® series available from Exxon Chemical, Shellsol series available from Shell.

The volatile silicone compounds useful herein include polyalkyl or polyaryl siloxanes with the following structure (I):

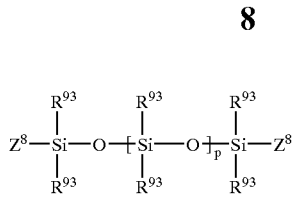

wherein $R^{93}$ is independently alkyl or aryl, and x is an integer from about 0 to about 5. $Z^8$ represents groups which block the ends of the silicone chains. Preferably, $R^{93}$ groups include methyl, ethyl, propyl, phenyl, methylphenyl and phenylmethyl, $Z^8$ groups include hydroxy, methyl, methoxy, ethoxy, propoxy, and aryloxy. More preferably, $R^{93}$ groups and $Z^8$ groups are methyl groups. The preferred volatile silicone compounds are hexamethyidisiloxane, octamethyltrisiloxane, decamethyltetrasiloxane, hexadecamethylheptasiloxane. Commercially available volatile silicone compounds useful herein include octamethyltrisiloxane with tradename SH200C-1cs, decamethyltetrasiloxane with tradename SH200C-1.5cs, hexadecamethylheptasiloxane with tradename SH200C-2cs, all available from Dow Corning.

The volatile silicone compounds useful herein also include a cyclic silicone compound having the formula:

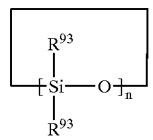

wherein $R^{93}$ is independently alkyl or aryl, and n is an integer of from 3 to 7. Preferably, R93 groups include methyl, ethyl, propyl, phenyl, methylphenyl and phenylmethyl. More preferably, $R^{93}$ groups are methyl groups. The preferred volatile silicone compounds are octamethylcyclotetrasiloxane, decamethylcyclopentasiloxane, tetradecamethylcyclohexasiloxane. Commercially available volatile silicone compounds useful herein include octamethylcyclotetrasiloxane with tradename SH244, decamethylcyclopentasiloxane with tradename DC 345 all available from Dow Corning.

Frizz Control Agent

The compositions of the present invention comprise a frizz control agent. The frizz control agent useful herein is believed to provide improved frizz control benefit and other conditioning benefits such as moisturized feel. The frizz control agent can be included in the composition of the present invention at a level by weight of, preferably from about 0.1% to about 20%, more preferably from about 0.5% to about 15%, even more preferably from about 1% to about 10%.

The frizz control agent useful herein is selected from the group consisting of (i), (ii), and (iii).

(i) PEG-modified glycerides having the structure:

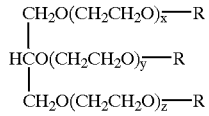

wherein one or more of the R groups is selected from saturated or unsaturated fatty acid moieties derived from animal or vegetable oils such as palmitic acid, lauric acid, oleic acid or linoleic acid wherein the fatty acid moieties have a carbon length chain of from 12 and 22, any other R groups are hydrogen, x, y, z are independently zero or more, the average sum of x+y+z (the degree of ethoxylation) is equal to from about 10 to about 45.

Preferably, the PEG-modified glycerides have an HLB value of about 20 or less, more preferably about 15 or less, still preferably about 11 or less.

Preferably, the PEG-modified glycerides have from 2 to 3 fatty acid R groups, more preferred are 3 fatty acid R groups (PEG-modified triglycerides). Preferably, the average sum of x+y+z (the degree of ethoxylation) is equal to from about 20 to 30, more preferred is an average sum of 25. Most preferred are PEG-substituted triglycerides having 3 oleic acid R groups, wherein the average degree of ethoxylation is about 25 (PEG-25 glyceryl trioleate).

Preferred commercially available PEG-modified triglycerides include Tagat TO®, Tegosoft GC, Tagat BL 276®, (all three manufactured by Goldschmidt Chemical Corporation) and Crovol A-40, Crovol M-40 (manufactured by Croda Corporation).

(ii) PEG-modified glyceryl fatty acid esters having the structure:

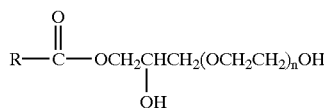

wherein R is an aliphatic group having from 12 to 22 carbon chain length, and n (the degree of ethoxylation) has an average value of from 5 to 40.

Preferably, the PEG-modified glyceryl fatty acid esters have an HLB value of about 20 or less, more preferably about 15 or less, still preferably about 11 or less.

Preferably, n has an average value of from about 15 to about 30, more preferred is an average value of from about 20 to about 30, and most preferably has an average value of 20. Preferred PEG-modified glyceryl fatty acid esters include PEG-30 glyceryl stearate and PEG-20 glyceryl stearate.

Preferred commercially available PEG-modified glyceryl fatty acid esters include Tagat S® and Tagat S 2® (manufactured by Goldschmidt Chemical Corporation).

(iii) mixtures thereof.

Additional Frizz Control Agent

The compositions of the present invention may comprise an additional frizz control agent selected from the group consisting of (i), (ii), (iii), (iv), and (v).

(i) dimethicone copolyols having the structure:

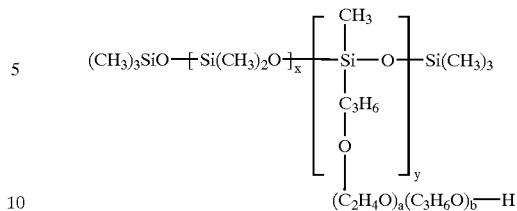

wherein x is an integer from 1 to 2000, y is an integer from 1 to 1000, a is zero or greater, b is zero or greater, the average sum of a+b is at least 1, and having an HLB value of about 20 or less.

Preferably the dimethicone copolyols have an HLB of about 15 or less and more preferably the dimethicone copolyols have an HLB of about 11 or less. Preferably x is an integer from 1 to 1000, y is an integer from 1 to 200. Preferably, a is an integer from 0 to 100, b is an integer from 0 to 100, the average sum of a+b is from 1 to 200, the ratio of propylene oxide substituents (b) to ethylene oxide substituents (a) is at least about 2:1, more preferably at least about 3:1, even more preferably at least about 4:1, and most preferably the dimethicone copolyols have only propylene oxide substituents and no ethylene oxide substituents. Preferred commercially available comb type dimethicone copolyols, useful herein, include Abil B 8852®, and Abil B 8873® (manufactured by the Goldschmidt Chemical Corporation).

(ii) dimethicone copolyols having the structure:

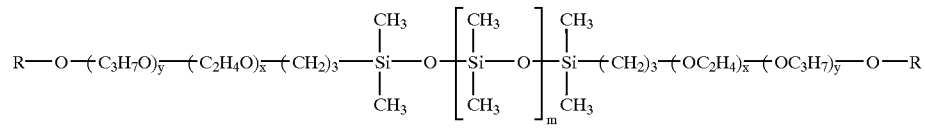

wherein R is selected from the group consisting of hydrogen, methyl, and combinations thereof, m is an integer from 1 to 2000, x is independently zero or greater, y is independently zero or greater, wherein the dimethicone copolyol has at least one ethylene oxide and/or propylene oxide, and has an HLB value of about 20 or less.

Preferably R is hydrogen, and the dimethicone copolyols have an HLB of about 15 or less and more preferably the dimethicone copolyols have an HLB of about 11 or less. Preferably m is an integer from 1 to 1000, more preferably from 1 to 500. Preferably, x is an integer from 0 to 100, y is an integer from 0 to 100, wherein the dimethicone copolyol has from 1 to 200 of ethylene oxide units and/or propylene oxide units. Preferably the ratio of propylene oxide substituents (y) to ethylene oxide substituents (x) is at least about 2:1, more preferably at least about 3:1, even more preferably at least about 4:1, and most preferably the dimethicone copolyols have only propylene oxide substituents and no ethylene oxide substituents. A preferred commercially available linear type dimethicone copolyol, useful herein, is Abil B 8830® (manufactured by the Goldschmidt Chemical Corporation).

(iii) polypropylene glycol

Polypropylene glycol useful herein has a weight average molecular weight of preferably from about 200 g/mol to about 100,000 g/mol, more preferably from about 1,000 g/mol to about 60,000 g/mol. Without intending to be limited by theory, it is believed that the polypropylene glycol herein deposits onto, or is absorbed into hair to act as a moisturizer buffer, and/or provides one or more other desirable hair conditioning benefits. As used herein, the term "polypropylene glycol" includes single-polypropylene glycol-chain segment polymers, and multi-polypropylene glycol-chain segment polymers. The general structure of branched polymers such as the multi-polypropylene glycol-chain segment polymers herein are described, for example, in "Principles of Polymerization," pp. 17–19, G. Odian, (John Wiley & Sons, Inc., $3^{rd}$ ed., 1991).

The polypropylene glycol herein are typically polydisperse polymers. The polypropylene glycols useful herein have a polydispersity of from about 1 to about 2.5, preferably from about 1 to about 2, and more preferably from about 1 to about 1.5. As used herein, the term "polydispersity" indicates the degree of the molecular weight distribution of the polymer sample. Specifically, the polydispersity is a ratio, greater than 1, equal to the weight average molecular weight divided by the number average molecular weight. For a further discussion about polydispersity, see "Principles of Polymerization," pp. 20–24, G. Odian, (John Wiley & Sons, Inc., $3^{rd}$ ed., 1991).

The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition. The solubility in water of the polypropylene glycol herein may be chosen by the artisan according to a variety of factors. Accordingly, for a leave-on hair care composition, it is preferred that the polypropylene glycol herein be a water-soluble polypropylene glycol. Solubility information is readily available from polypropylene glycol suppliers, such as Sanyo Kasei (Osaka, Japan). However, the present invention may also take the form of a rinse-off hair care composition. Without intending to be limited by theory, it is believed that in such a composition, a water-soluble polypropylene glycol may be too easily washed away before it effectively deposits on hair and provides the desired benefit(s). For such a composition, a less soluble, or even a water-insoluble polypropylene glycol is therefore preferred. Accordingly, for a rinse-off hair care composition, it is preferred that the polypropylene glycol herein has a solubility in water at 25° C. of less than about 1 g/100 g water, more preferably a solubility in water of less than about 0.5 g/100 g water, and even more preferably a solubility in water of less than about 0.1 g/100 g water.

Preferably the polypropylene glycol is selected from the group consisting of a single-polypropylene glycol-chain segment polymer, a multi-polypropylene glycol-chain segment polymer, and mixtures thereof, more preferably selected from the group consisting of a single-polypropylene glycol-chain segment polymer of Formula I, below, a multi-polypropylene glycol-chain segment polymer of Formula II, below, and mixtures thereof.

Accordingly, a highly preferred single-polypropylene glycol-chain segment polymer has the formula:

$$HO-(C_3H_6O)_a H \qquad (III),$$

wherein a is a value from about 4 to about 400, preferably from about 20 to about 100, and more preferably from about 20 to about 40.

The single-polypropylene glycol-chain segment polymer useful herein is typically inexpensive, and is readily available from, for example, Sanyo Kasei (Osaka, Japan), Dow Chemicals (Midland, Mich., USA), Calgon Chemical, Inc. (Skokie, Ill., USA), Arco Chemical Co. (Newton Square Pa., USA), Witco Chemicals Corp. (Greenwich, Conn., USA), and PPG Specialty Chemicals (Gurnee, Ill., USA).

A highly preferred multi-polypropylene glycol-chain segment polymer has the formula:

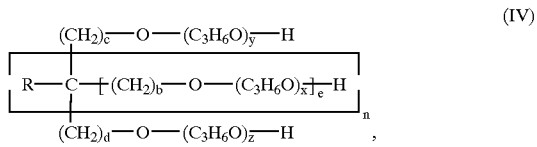

(IV)

wherein n is a value from about 0 to about 10, preferably from about 0 to about 7, and more preferably from about 1 to about 4. In Formula IV, each R" is independently selected from the group consisting of H, and $C_1$–$C_{30}$ alkyl, and preferably each R" is independently selected from the group consisting of H, and $C_1$–$C_4$ alkyl. In Formula IV, each b is independently a value from about 0 to about 2, preferably from about 0 to about 1, and more preferably b=0. Similarly, c and d are independently a value from about 0 to about 2, preferably from about 0 to about 1. However, the total of b+c+d is at least about 2, preferably the total of b+c+d is from about 2 to about 3. Each e is independently a value of 0 or 1, if n is from about 1 to about 4, then e is preferably equal to 1. Also in Formula IV, x, y, and z is independently a value of from about 1 to about 120, preferably from about 7 to about 100, and more preferably from about 7 to about 100, where x+y+z is greater than about 20.

Examples of the multi-polypropylene glycol-chain segment polymer of Formula IV which is especially useful herein includes polyoxypropylene glyceryl ether (n=1, R'=H, b=0, c and d=1, e=1, and x, y, and z independently indicate the degree of polymerization of their respective polypropylene glycol-chain segments; available as New Pol GP-4000, from Sanyo Kasei, Osaka, Japan), polypropylene trimethylol propane (n=1, R'=$C_2H_5$, b=1, c and d=1, e=1, and x, y, and z independently indicate the degree of polymerization of their respective polypropylene glycol-chain segments), polyoxypropylene sorbitol (n=4, each R'=H, b=0, c and d=1, each e=1, and y, z, and each x independently indicate the degree of polymerization of their respective polypropylene glycol-chain segments; available as New Pol SP-4000, from Sanyo Kasei, Osaka, Japan), and PPG-10 butanediol (n=0, c and d=2, and y+z=10; available as Probutyl DB-10, from Croda, Inc., of Parsippany, N.J., U.S.A.).

In a preferred embodiment, one or more of the propylene repeating groups in the polypropylene glycol is an isopropyl oxide repeating group. More preferably one or more of the propylene oxide repeating groups of the polypropylene glycol of Formula III and/or the polypropylene glycol of Formula IV is an isopropyl oxide repeating group. Even more preferably, substantially all of the propylene oxide repeating groups of the polypropylene glycol of Formula III and/or the polypropylene glycol of Formula IV are isopropyl oxide repeating groups. Accordingly, a highly preferred single-polypropylene glycol-chain segment polymer has the formula:

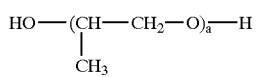

wherein a is defined as described above for Formula III. Similarly, a highly preferred multi-polypropylene glycol-chain segment polymer has the formula:

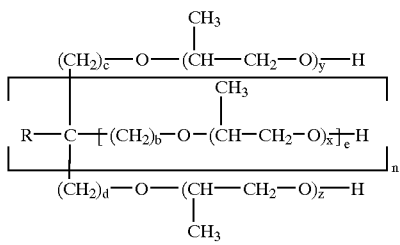

wherein n, R", b, c, d, e, x, y, and z are defined as above, for Formula IV. It is recognized that the isopropyl oxide repeating groups may also correspond either alone, or in combination with the above depicted, to:

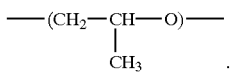

The polypropylene glycol useful herein is readily available from, for example, Sanyo Kasei (Osaka, Japan) as New pol PP-2000, New pol PP-4000, New pol GP-4000, and New pol SP-4000, from Dow Chemicals (Midland, Mich., USA), from Calgon Chemical, Inc. (Skokie, Ill., USA), from Arco Chemical Co. (Newton Square Pa., USA), from Witco Chemicals Corp. (Greenwich, Conn., USA), and from PPG Specialty Chemicals (Gurnee, Ill., USA).

(vi) Pentaerythritol ester oils useful herein are those having the formula:

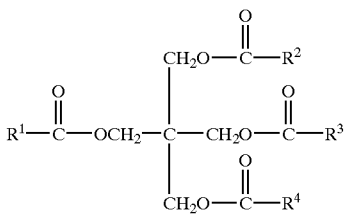

wherein $R^1$, $R^2$, $R^3$, and $R^4$, independently, are branched, straight, saturated, or unsaturated alkyl, aryl, and alkylaryl groups having from 1 to about 30 carbons. Preferably, $R^1$, $R^2$, $R^3$, and $R^4$, independently, are branched, straight, saturated, or unsaturated alkyl groups having from about 8 to about 22 carbons. More preferably, $R^1$, $R^2$, $R^3$ and $R^4$ are defined so that the molecular weight of the compound is from about 800 to about 1200.

Particularly useful pentaerythritol ester oils herein include pentaerythritol tetraisostearate, pentaerythritol tetraoleate, and mixtures thereof. Such compounds are available from Kokyu Alcohol with tradenames KAKPTI, KAKTTI.

(v) mixtures thereof.

The additional frizz control agent can be included in the composition of the present invention at a level by weight of, preferably from about 0.1% to about 20%, more preferably from about 0.5% to about 15%, even more preferably from about 1% to about 10%.

Thickening Agent

The compositions of the present invention may further comprise a thickening agent. The thickening agent is preferably included in the aqueous composition of the present invention. The thickening agent can be included in the compositions of the present invention at a level by weight of, preferably from about 0.01% to about 10%, more preferably from about 0.03% to about 8%, still preferably from about 0.1% to about 5%.

The thickening system useful herein is believed to provide The thickening agent useful herein can also provide appropriate viscosity and rheology properties to the composition, so that the composition of the present composition has a suitable viscosity, preferably from about 1,000 mpa·s to about 100,000 mPa·s, more preferably from about 2,000 mPa·s to about 50,000 mPa·s. The viscosity herein can be suitably measured by Brookfield RVT at 20 rpm at 20° C. using either spindle #4, 5, 6 or 7 depending on the viscosity and the characteristic of the composition.

The thickening agent useful herein are water soluble or water miscible polymers, have the ability to increase the viscosity of the composition, and are compatible with other components of the present invention.

Useful herein are carboxylic acid/carboxylate copolymers such as hydrophobically-modified cross-linked coplymers of carboxylic acid and alkyl carboxylate, and have an amphiphilic property. These carboxylic acid/carboxylate copolymers are obtained by copolymerizing 1) a carboxylic acid monomer such as acrylic acid, methacrylic acid, maleic acid, maleic anhydride, itaconic acid, fumaric acid, crotonic acid, or α-chloroacrylic acid, 2) a carboxylic ester having an alkyl chain of from 1 to about 30 carbons, and preferably 3) a crosslinking agent of the following formula:

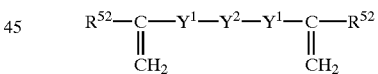

wherein $R^{52}$ is a hydrogen or an alkyl group having from about 1 to about 30 carbons; $Y^1$, indepedently, is oxygen, $CH_2O$, COO, OCO,

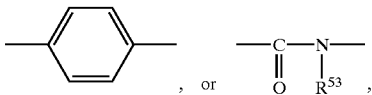

wherein $R^{53}$ is a hydrogen or an alkyl group having from about 1 to about 30 carbons; and $Y^2$ is selected from $(CH_2)_{m''}$, $(CH_2CH_2O)_{m''}$, or $(CH_2CH_2CH_2O)_{m''}$ wherein m" is an integer of from 1 to about 30.

Suitable carboxylic acid/carboxylate copolymers herein are acrylic acid/alkyl acrylate copolymers having the following formula:

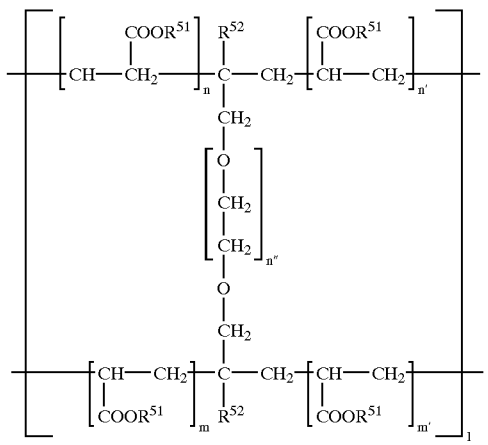

wherein $R^{51}$, independently, is a hydrogen or an alkyl of 1 to 30 carbons wherein at least one of $R^{51}$ is a hydrogen, $R^{52}$ is as defined above, n, n', m and m' are integers in which n+n'+m+m' is from about 40 to about 100, n" is an integer of from 1 to about 30, and l is defined so that the copolymer has a molecular weight of about 500,000 to about 3,000,000.

Commercially available carboxylic acid/carboxylate copolymers useful herein include: CTFA name Acrylates/C10-30 Alkyl Acrylate Crosspolymer having tradenames Pemulene TR-1, Pemulene TR-2, Carbopol 1342, Carbopol 1382, and Carbopol ETD 2020, all available from B. F. Goodrich Company.

Neutralizing agents may be included to neutralize the carboxylic acid/carboxylate copolymers herein. Nonlimiting examples of such neutralizing agents include sodium hydroxide, potssium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof.

Another thickening agents useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyethylene glycols having a molecular weight of more than about 1000 are useful herein. Useful are those having the following general formula:

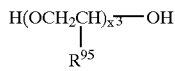

wherein $R^{95}$ is selected from the group consisting of H, methyl, and mixtures thereof. In the above structure, x3 has an average value of from about 1500 to about 25,000, preferably from about 2500 to about 20,000, and more preferably from about 3500 to about 15,000. When $R^{95}$ is H, these materials are polymers of ethylene oxide, which are also known as polyethylene oxides, polyoxyethylenes, and polyethylene glycols. Other useful polymers include the mixed polyethylene-polypropylene glycols, or polyoxyethylene-polyoxypropylene copolymer polymers. Polyethylene glycol polymers useful herein are PEG-2M wherein $R^{95}$ equals H and x3 has an average value of about 2,000 (PEG-2M is also known as Polyox WSR® N-10, which is available from Union Carbide and as PEG-2,000); PEG-5M wherein $R^{95}$ equals H and x3 has an average value of about 5,000 (PEG-5M is also known as Polyox WSR® N-35 and Polyox WSR® N-80, both available from Union Carbide and as PEG-5,000 and Polyethylene Glycol 300,000); PEG-7M wherein $R^{95}$ equals H and x3 has an average value of about 7,000 (PEG-7M is also known as Polyox WSR® N-750 available from Union Carbide); PEG-9M wherein $R^{95}$ equals H and x3 has an average value of about 9,000 (PEG 9-M is also known as Polyox WSR® N-3333 available from Union Carbide); and PEG-14 M wherein $R^{95}$ equals H and x3 has an average value of about 14,000 (PEG-14M is also known as Polyox WSR® N-3000 available from Union Carbide).

Commercially available another thickening agents highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxypropyl cellulose with tradename KLUCEL, all supplied by Herculus, hydroxyethyl cellulose with tradename NATROSOL 250HBR and 250 MBR available from Aqualon, ethylene oxide and/or propylene oxide based polymers with tradenames CARBOWAX PEGs, POLYOX WASRs, and UCON FLUIDS, all supplied by Amerchol.

Another thickening agent useful herein is a hydrophobically modified cellulose ethers. The hydrophobically modified cellulose ethers useful herein are preferably nonionic polymers. The hydrophobically modified cellulose ethers useful herein comprise a hydrophilic cellulose backbone and a hydrophobic substitution group. The hydrophilic cellulose backbone has a sufficient degree of nonionic substitution to cellulose to be water soluble. Such hydrophilic cellulose backbone is selected from the group consisting of methyl cellulose, hydroxymethyl cellulose, hydroxyethyl cellulose, hydroxyethyl ethylcellulose, hydroxypropyl cellulose, hydroxypropyl methylcellulose, and mixtures thereof. The amount of nonionic substitution is not critical, so long as there is an amount sufficient to assure that the hydrophilic cellulose backbone is water soluble. The hydrophilic cellulose backbone has a molecular weight of about less than 800,000, preferably from about 20,000 to about 700,000, or from about 75 D. P. to about 2500 D. P. Further, where a high viscosity building effect is not desirable, a lower molecular weight cellulose backbone is preferred. One of the preferred hydrophilic cellulose backbone is hydroxyethyl cellulose having a molecular weight of from about 50,000 to about 700,000. Hydroxyethyl cellulose of this molecular weight is known to be one of the most hydrophilic of the materials contemplated. Thus, hydroxyethyl cellulose can be modified to a greater extent than other hydrophilic cellulose backbones.

The hydrophilic cellulose backbone is further substituted with a hydrophobic substitution group via an ether linkage to render the hydrophobically modified cellulose ether to have less than 1% water solubility, preferably less than 0.2% water solubility. The hydrophobic substitution group is selected from a straight or branched chain alkyl group of from about 10 to about 22 carbons; wherein the ratio of the hydrophilic groups in the hydrophilic cellulose backbone to the hydrophobic substitution group being from about 2:1 to about 1000:1, preferably from about 10:1 to about 100:1.

Commercially available hydrophobically modified cellulose ethers useful herein include: cetyl hydroxyethylcellulose having tradenames NATROSOL PLUS 330CS and POLYSURF 67, both available from Aqualon Company, Del., USA, having cetyl group substitution of about 0.4% to about 0.65% by weight of the entire polymer.

Amphoteric Conditioning Polymer

The compositions of the present invention may further comprise an amphoteric conditioning polymer. The amphoteric conditioning polymer is preferably included in an aqueous composition of the present invention. The amphoteric conditioning polymer can be included in the compositions of the present invention at a level by weight of, preferably from about 0.01% to about 10%, more preferably from about 0.1% to about 8%, still preferably from about 0.5% to about 5%.

The amphoteric conditioning polymers herein are those compatible with the thickening agent and other components, and which provide conditioning benefit to the hair. Although some of the amphoteric conditioning polymers herein may have some hair holding or hair fixative properties, such hair holding or hair fixative properties are not a requirement for the amphoteric conditioning polymers herein. The amphoteric conditioning polymers useful herein are those including at least one cationic monomer and at least one anionic monomer; the cationic monomer being quaternary ammonium, preferably dialkyl diallyl ammonium chloride or carboxylamidoalkyl trialkyl ammonium chloride; and the anionic monomer being carboxylic acid. The amphoteric conditioning polymers herein may include nonionic monomers such as acrylamine, methacrylate, or ethacrylate. Further, the amphoteric conditioning polymers useful herein do not contain betanized monomers.

Useful herein are polymers with the CTFA name Polyquaternium 22, Polyquaternium 39, and Polyquaternium 47. Such polymers are, for example, copolymers consisting of dimethyldiallyl ammonium chloride and acrylic acid, terpolymers consisting of dimethyidiallyl ammonium chloride and acrylamide, and terpolymers consisting of acrylic acid methacrylamidopropyl trimethylammonium chloride and methyl acrylate such as those of the following formula wherein the ratio of $n^6:n^7:n^8$ is 45:45:10:

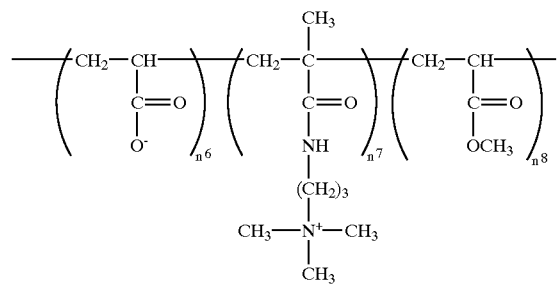

Highly preferred commercially available amphoteric conditioning polymers herein include Polyquaternium 22 with tradenames MERQUAT 280, MERQUAT 295, Polyquaternium 39 with tradenames MERQUAT PLUS 3330, MERQUAT PLUS 3331, and Polyquaternium 47 with tradenames MERQUAT 2001, MERQUAT 2001N, all available from Calgon Corporation.

Also useful herein are polymers resulting from the copolymerisation of a vinyl monomer carrying at least one carboxyl group, such as acrylic acid, methacrylic acid, maleic acid, itaconic acid, fumaric acid, crotonic acid, or alphachloroacrylic acid, and a basic monomer which is a substituted vinyl compound containing at least one basic nitrogen atom, such as dialkylaminoalkyl methacrylates and acrylates and dialkylaminoalkylmethacrylamides and acrylamides.

Also useful herein are polymers containing units derived from:
i) at least one monomer chosen from amongst acrylamides or methacrylamides substituted on the nitrogen by an alkyl radical,
ii) at least one acid comonomer containing one or more reactive carboxyl groups, and
iii) at least one basic comonomer, such as esters, with primary, secondary and tertiary amine substituents and quaternary ammonium substituents, of acrylic and methacrylic acids, and the product resulting from the quaternisation of dimethylaminoethyl methacrylate with dimethyl or diethyl sulfate.

The N-substituted acrylamides or methacrylamides which are most particularly preferred are the groups in which the alkyl radicals contain from 2 to 12 carbon atoms, especially N-ethylacrylamide, N-tert.-butylacrylamide, N-tert.-octylacrylamide, N-octylacrylamide, N-decylacrylamide and N-dodecylacrylamide and also the corresponding methacrylamides. The acid comonomers are chosen more particularly from amongst acrylic, methacrylic, crotonic, itaconic, maleic and fumaric acids and also the alkyl monoesters of maleic acid or fumaric acid in which alkyl has 1 to 4 carbon atoms.

The preferred basic comonomers are aminoethyl, butylaminoethyl, N,N'-dimethylaminoethyl and N-tert.-butylaminoethyl methacrylates. Commercially available amphoteric conditioning polymers herein include octylacrylamine/acrylates/butylaminoethyl methacrylate copolymers with the tradenames AMPHOMER, AMPHOMER SH701, AMPHOMER 28-4910, AMPHOMER LV71, and AMPHOMER LV47 supplied by National Starch & Chemical.

Humectant

The compositions of the present invention may further comprise a humectant. The humectant is preferably included in an aqueous composition of the present invention. The humectant can be included in the compositions of the present invention at a level by weight of, preferably from about 0.1% to about 20%, more preferably from about 0.3% to about 10%, still preferably from about 0.5% to about 5%.

The humectants herein are selected from the group consisting of polyhydric alcohols, water soluble alkoxylated nonionic polymers, and mixtures thereof.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosin phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Commercially available humectants herein include: glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from lchimaru Pharcos; sodium adenosin phophate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Torrien; and polyethylene glycols with the tradename CARBOWAX series available from Union Carbide.

Aqueous Carrier

The compositions of the present invention may further comprise an aqueous carrier. The aqueous carrier is included in an aqueous composition of the present invention. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the aqueous compositions of the present invention comprise from about 10% to about 99%, preferably from about 20% to about 80%, and more preferably from about 30% to about 70% water.

Non-Aqueous Composition

The hair conditioning composition of the present invention can be a non-aqueous composition comprising by weight:
(1) from about 1% to about 30%, preferably from about 3% to about 25%, more preferably from about 5% to about 20%, of the non-volatile silicone compound;
(2) from about 50% to about 98.9%, preferably from about 55% to about 98%, more preferably from about 70% to about 95%, of the volatile compound as non-aqueous carrier; and
(3) from about 0.1% to about 20%, preferably from about 0.5 to about 15%, more preferably from about 1% to about 10%, of the frizz control agent.

The non-aqueous compositions may further comprise by weight from about 0.1% to about 20%, preferably from about 0.5% to about 15%, more preferably from about 1% to about 10%, of the additional frizz control agent.

Aqueous Composition

The hair conditioning composition of the present invention can be an aqueous composition comprising by weight:
(1) from about 0.5% to about 20%, preferably from about 0.75% to about 15%, more preferably from about 1% to about 10%, of the non-volatile silicone compound;
(2) from about 5% to about 70%, preferably from about 10% to about 65%, more preferably from about 20% to about 50%, of the volatile compound;
(3) from about 0.1% to about 20%, preferably from about 0.5% to about 15%, more preferably from about 1% to about 10%, of the frizz control agent;
(4) from about 0.01% to about 10%, preferably from about 0.03% to about 8%, more preferably from about 0.1% to about 5%, of a thickening agent; and
(5) an aqueous carrier.

The aqueous composition of the present invention preferably further comprises by weight:
(6) from about 0.01% to about 10%, preferably from about 0.1% to about 8%, more preferably from about 0.5% to about 5%, of the amphoteric conditioning polymer; and
(7) from about 0.1% to about 20%, preferably from about 0.3% to about 10%, more preferably from about 0.5% to about 5%, of the humectant.

The aqueous compositions may further comprise by weight from about 0.1% to about 20%, preferably from about 0.5% to about 15%, more preferably from about 1% to about 10%, of the additional frizz control agent.

Water-Soluable Styling Polymer

The aqueous composition of the present invention can contain water-soluble styling polymers. Such aqueous conditioning composition containing water-soluble styling polymers can provide well-balanced conditioning and styling benefits, i.e., can provide styling benefits such as hair style achievement, and hold and retention, while delivering improved conditioning benefits such as frizz control benefit, smoothness, softness, and reduction of friction while reducing sticky and greasy feeling.

The water-soluble polymers can be included in the composition at a level by weight of preferably from about 0.01% to about 10%, more preferably from about 0.05% to about 5%, still more preferably from about 0.1% to about 3%.

The water-soluble styling polymers useful herein includes; for example, vinylpyrrolidone homopolymers such as polyvinylpyrrolidone; vinylpyrrolidone copolymers such as polyvinylpyrrolidone/vinyl acetate copolymer and polyvinylpyrrolidone/dimethylaminoethylmethacrylate copolymer; dimethylaminoethylmethacrylate copolymer; polyquaterniums such as polyquaternium-11 and polyquaternium-4; alkyl esters of PVM/MA Copolymer such as ethyl ester of PVM/MA Copolymer and butyl ester of PVM/MA Copolymer; quaternized celluloses; acrylate homopolymers and acrylate copolymers such as carbomers; VA/Crotonates/Vinyl Neodecanoate; and mixtures thereof. Some water-soluble styling polymers described herein can also be used as the "THICKENING AGENT" described above.

Among them, preferred are vinylpyrrolidone copolymers in view of improved styling benefits.

The vinylpyrrolidone copolymers useful herein are those which comprise monomers other than vinylpyrrolidone. Non-limiting examples of vinylpyrrolidone copolymers useful herein include polyvinylpyrrolidone/acrylates/lauryl methacrylate copolymer, polyvinylpyrrolidone/dimethiconylacrylate/polycarbamyl/polyglycol ester, polyvinylpyrrolidone/dimethylaminoethylmethacrylate copolymer, polyvinylpyrrolidone/dimethylaminoethylmethacrylate/polycarbamylpolyglycol ester, polyvinylpyrrolidone/DMAPA acrylates copolymer, polyvinylpyrrolidone/eicosene copolymer, polyvinylpyrrolidone/hexadecene copolymer, polyvinylpyrrolidone/polycarbamyl polyglycol ester, polyvinylpyrrolidone/vinyl acetate copolymer, polyvinylpyrrolidone/vinyl acetate/itaconic acid copolymer, polyvinylpyrrolidone/vinyl acetate/vinyl propionate copolymer, and polyvinylpyrrolidone/vinyl caprolactam/DMAPA acrylates copolymer.

Preferably, the copolymer of pyrrolidone useful herein is a nonionic copolymer in view of less deteriorating conditioning benefits and better compatibility with thickening agent, especially carboxylic acid/carboxylate copolymer thickening agent.

Preferably, polyvinylpyrrolidone/vinyl acetate copolymer and polyvinylpyrrolidone/vinyl acetate/vinyl propionate copolymer are used in the compositions of the present invention, and more preferably, polyvinylpyrrolidone/vinyl acetate copolymer is used in the compositions of the present invention in view of less deteriorating conditioning benefits and better compatibility with thickening agent, especially carboxylic acid/carboxylate copolymer thickening agent. In the polyvinylpyrrolidone/vinyl acetate copolymer, the mole ratio of vinylpyrrolidone monomer to vinyl acetate monomer may be preferably from about 1:9 to about 9:1, more preferably from about 5:5 to about 8:2.

Commercially available vinylpyrrolidone copolymers useful herein include: CTFA name polyvinylpyrrolidone/vinyl acetate copolymer having tradenames Luviskol VA28E, Luviskol VA37E, Luviskol VA55E, Luviskol VA64E, Luviskol VA73E, Luviskol VA37HM, Luviskol VA64 Powder, Luviskol VA64W, and Luviskol VA73W, all available from BASF, and PVP/VA E series, I series, S-630, all available from ISP; CTFA name polyvinylpyrrolidone/vinyl acetate/vinyl propionate copolymer having tradename Luviskol VAP343E available from BASF; CTFA name polyvinylpyrrolidone/acrylates/lauryl methacrylate copolymer having tradename Acrylidone LM available from ISP; CTFA name polyvinylpyrrolidone/dimethiconylacrylate/polycarbamyl/polyglycol ester having tradename Pecogel S-1120 available from Phoenix; CTFA name polyvinylpyrrolidone/dimethylaminoethylmethacrylate copolymer having tradename Copolymer 845, Copolymer 937, and Copolymer 958, all available from ISP; CTFA name polyvinylpyrrolidone/dimethylaminoethylmethacrylate/polycarbamylpolyglycol ester having tradename Pecogel GC-310 and Pecogel GC-1110 available from Phoenix; CTFA name polyvinylpyrrolidone/DMAPA acrylates copolymer having tradename ACP-1163 available from ISP; CTFA name polyvinylpyrrolidone/eicosene copolymer having tradename Antaron V-220 and Ganex V-220 available from ISP; CTFA name polyvinylpyrrolidone/hexadecene copolymer having tradename Antaron V-216 and Ganex V-216 available from ISP; CTFA name polyvinylpyrrolidone/polycarbamyl polyglycol ester having tradename Pecogel A-12 and Pecogel H series available from Phoenix; CTFA name polyvinylpyrrolidone/vinyl caprolactam/DMAPA acrylates copolymer having tradename ACP-1189 available from ISP.

Additional Components

The compositions of the present invention may contain additional components such as high melting fatty compounds, cationic conditioning agents consisting of cationic surfactants, cationic polymers, and mixtures thereof, nonionic surfactants, UV absorbers, and so on.

High Melting Fatty Compound

The compositions of the present invention may contain a high melting point fatty compound. The high melting point fatty compound can be included in the aqueous composition at a level by weight of, preferably from about 0.1% to about 20%, more preferably from about 0.5% to about 15%, even more preferably from about 1% to about 10%.

The high melting point compound useful herein have a melting point of at least about 25° C. selected from the group consisting of fatty alcohols, fatty acids, fatty alcohol derivatives, fatty acid derivatives, hydrocarbons, steroids, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

It is believed that these high melting point compounds cover the hair surface and reduce friction, thereby resulting in providing smooth feel on the hair and ease of combing.

The fatty alcohols useful herein are those having from about 14 to about 30 carbon atoms, preferably from about 16 to about 22 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$–$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

Hydrocarbons useful herein include compounds having at least about 20 carbons.

Steroids useful herein include compounds such as cholesterol.

High melting point compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Commercially available high melting point compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy); and cholesterol having tradename NIKKOL AGUASOME LA available from Nikko.

Cationic Conditioning Agent

The compositions of the present invention may contain a cationic conditioning agent. The cationic conditioning agent is preferably included in the aqueous composition of the present invention. The cationic conditioning agent can be included in the aqueous composition at a level by weight of, preferably from about 0.1% to about 20%, more preferably from about 0.5% to about 15%, even more preferably from about 1% to about 10%.

Preferably, the cationic conditioning agent is selected from the group consisting of cationic surfactants, cationic polymers, and mixtures thereof. Cationic conditioning agents are selected according to the compatibility with other components, and the desired characteristic of the product. Preferred herein is a cationic surfactant.

Cationic Surfactant

Among the cationic surfactants useful herein are those corresponding to the general formula (I):

wherein at least one of $R^{71}$, $R^{72}$, $R^{73}$ and $R^{74}$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^{71}$, $R^{72}$, $R^{73}$ and $R^{74}$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^{71}$, $R^{72}$, $R^{73}$ and $R^{74}$ are independently selected from $C_1$ to about $C_{22}$ alkyl. Nonlimiting examples of cationic surfactants useful in the present invention include the materials having the following CTFA designations: quaternium-8, quaternium-14, quaternium-18, quaternium-18 methosulfate, quaternium-24, and mixtures thereof.

Among the cationic surfactants of general formula (I), preferred are those containing in the molecule at least one alkyl chain having at least 16 carbons. Nonlimiting examples of such preferred cationic surfactants include: behenyl trimethyl ammonium chloride available, for example, with tradename INCROQUAT TMC-80 from Croda and ECONOL TM22 from Sanyo Kasei; cetyl trimethyl ammonium chloride available, for example, with tradename CA-2350 from Nikko Chemicals, hydrogenated tallow alkyl trimethyl ammonium chloride, dialkyl (14–18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^{71}$–$R^{74}$ radicals contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Preferred hydrophilically substituted cationic surfactants include those of the formula (II) through (VIII) below:

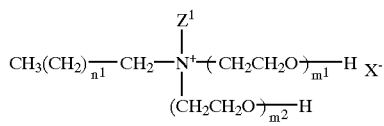
(II)

wherein $n^1$ is from 8 to about 28, $m^1+m^2$ is from 2 to about 40, $Z^1$ is a short chain alkyl, preferably a $C_1$–$C_3$ alkyl, more preferably methyl, or $(CH_2CH_2O)_{m3}H$ wherein $m^1+m^2+m^3$ is up to 60, and X is a salt forming anion as defined above;

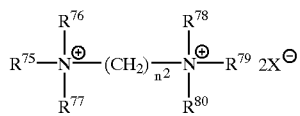
(III)

wherein $n^2$ is 1 to 5, one or more of $R^{75}$, $R^{76}$, and $R^{77}$ are independently an $C_1$–$C_{30}$ alkyl, the remainder are $CH_2CH_2OH$, one or two of $R^{78}$, $R^{79}$, and $R^{80}$ are independently an $C_1$–$C_{30}$ alkyl, and remainder are $CH_2CH_2OH$, and X is a salt forming anion as mentioned above;

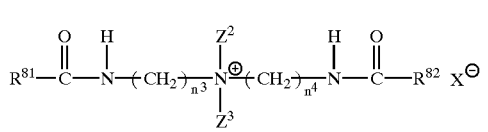
(IV)

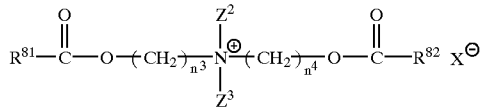
(V)

wherein, independently for formulae (IV) and (V), $Z^2$ is an alkyl, preferably $C_1$–$C_3$ alkyl, more preferably methyl, and $Z^3$ is a short chain hydroxyalkyl, preferably hydroxymethyl or hydroxyethyl, $n^3$ and $n^4$ independently are integers from 2 to 4, inclusive, preferably from 2 to 3, inclusive, more preferably 2, $R^{81}$ and $R^{82}$, independently, are substituted or unsubstituted hydrocarbyls, $C_{12}$–$C_{20}$ alkyl or alkenyl, and X is a salt forming anion as defined above;

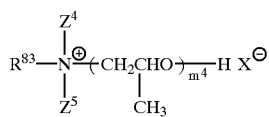
(VI)

wherein $R^{83}$ is a hydrocarbyl, preferably a $CD_1$–$C_3$ alkyl, more preferably methyl, $Z^4$ and $Z^5$ are, independently, short chain hydrocarbyls, preferably $C_2$–$C_4$ alkyl or alkenyl, more preferably ethyl, $m^4$ is from 2 to about 40, preferably from about 7 to about 30, and X is a salt forming anion as defined above;

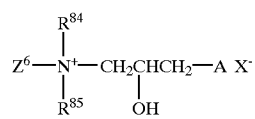
(VII)

wherein $R^{84}$ and $R^{85}$, independently, are $C_1$–$C_3$ alkyl, preferably methyl, $Z^6$ is a $C_{12}$–$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

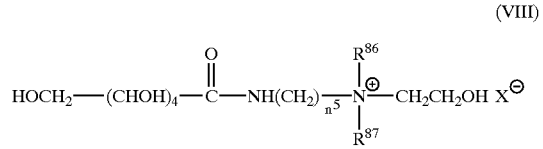
(VIII)

wherein $n^5$ is 2 or 3, $R^{86}$ and $R^{87}$, independently are $C_1$–$C_3$ hydrocarbyls preferably methyl, and X is a salt forming anion as defined above. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemical, MACKPRO KLP, MACKPRO WLW, MACKPRO MLP, MACKPRO NSP, MACKPRO NLW, MACKPRO WWP, MACKPRO NLP, MACKPRO SLP from Mcintyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas.

Amines are suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyidiethylamine, stearamidoethyldimethylamine, palmitamidopropyidimethylamine, palmitamidopropyldiethylamine, palmitamidoethyldiethylamine, palmitamidoethyldimethylamine, behenamidopropyidimethylamine, behenamidopropyldiethylamine, behenamidoethyldiethylamine, behenamidoethyidimethylamine, arachidamidopropyldimethylamine, arachidamidopropyldiethylamine, arachidamidoethyldiethylamine, arachidamidoethyidimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. Useful amines in the present invention are disclosed in U.S. Pat. No. 4,275,055, Nachtigal, et al.

These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Cationic Polymer

Cationic polymers are also useful herein. As used herein, the term "polymer" shall include materials whether made by polymerization of one type of monomer or made by two (i.e., copolymers) or more types of monomers.

Preferably, the cationic polymer is a water soluble cationic polymer. By "water soluble" cationic polymer, what is meant is a polymer which is sufficiently soluble in water to form a substantially clear solution to the naked eye at a concentration of 0.1% in water (distilled or equivalent) at 25° C. The preferred polymer will be sufficiently soluble to form a substantially clear solution at 0.5% concentration, more preferably at 1.0% concentration.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula $R^{88}X$ wherein $R^{88}$ is a short chain alkyl, preferably a $C_1$–$C_7$ alkyl, more preferably a $C_1$–$C_3$ alkyl, and X is a salt forming anion as defined above.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256.

Other cationic polymers that can be used include polysaccharide polymers, such as cationic cellulose derivatives and cationic starch derivatives.

Cationic polysaccharide polymer materials suitable for use herein include those of the formula:

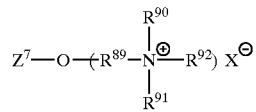

wherein: $Z^7$ is an anhydroglucose residual group, such as a starch or cellulose anhydroglucose residual, $R^{89}$ is an alkylene oxyalkylene, polyoxyalkylene, or hydroxyalkylene group, or combination thereof, $R^{90}$, $R^{91}$, and $R^{92}$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^{90}$, $R^{91}$ and $R^{92}$) preferably being about 20 or less, and X is as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename) Polymer LM-®.

Other cationic polymers that can be used include cationic guar gum derivatives, such as guar hydroxypropyltrimonium chloride commercially available from Celanese Corp. in their Jaguar R series. Other materials include quaternary nitrogen-containing cellulose ethers as described in U.S. Pat. No. 3,962,418, and copolymers of etherified cellulose and starch as described in U.S. Pat. No. 3,958,581.

Particularly useful cationic polymers herein include Polyquaternium-7, Polyquaternium-10, Polyquaternium-24, and mixtures thereof.

Nonionic Surfactant

The hair conditioning composition of the present invention may contain a nonionic surfactant. The nonionic surfactant can be included in the composition of the present invention at a level by weight of, preferably from about 0.01% to about 10%, more preferably from about 0.05% to about 8%, still preferably from about 0.1% to about 5%.

Nonionic surfactants include those compounds produced by condensation of alkylene oxide groups, hydrophilic in nature, with an organic hydrophobic compound, which may be aliphatic or alkyl aromatic in nature.

Preferred nonlimiting examples of nonionic surfactants for use in the shampoo compositions include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configurations, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula [$R^1 R^2 R^3 N \rightarrow O$] where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula [RR'R"P$\rightarrow$O] where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R" are each alkyl or monohydroxyalkyl groups containing from about 1 to about 3 carbon atoms;

(6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties;

(7) alkyl polysaccharide (APS) surfactants (e.g. alkyl polyglycosides), examples of which are described in U.S. Pat. No. 4,565,647, which is incorporated herein by reference in its entirety, and which discloses APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside, which is commercially available from Henkel, ICI Americas, and Seppic; and (8) polyoxyethylene alkyl ethers such as those of the formula RO(CH$_2$CH$_2$O)$_n$H and polyethylene glycol (PEG) glyceryl fatty esters, such as those of the formula R(O)OCH$_2$CH(OH)CH$_2$(OCH$_2$CH$_2$)$_n$OH, wherein n is from 1 to about 200, preferably from about 20 to about 100, and R is an alkyl having from about 8 to about 22 carbon atoms.

Preferably, polyethylene glycol derivatives of glycerides as described in the above (8) are used as the nonionic surfactants in the composition of the present invention.

Polyethylene glycol derivatives of glycerides useful herein include any polyethylene glycol derivative of glycerides which are water-soluble and which are suitable for use in a hair conditioning composition. Suitable polyethylene glycol derivatives of glycerides for use herein include derivatives of mono-, di- and tri-glycerides and mixtures thereof.

One class of polyethylene glycol derivatives of glycerides suitable herein are those which conform to the general formula (I):

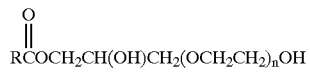

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms.

Suitable polyethylene glycol derivatives of glycerides can be polyethylene glycol derivatives of hydrogenated castor oil. For example, PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil. Preferred for use in the compositions herein is PEG-60 hydrogenated castor oil.

Other suitable polyethylene glycol derivatives of glycerides can be polyethylene glycol derivatives of stearic acid. For example, PEG-30 stearate, PEG-40 stearate, PEG-50 stearate, PEG-75 stearate, PEG-90 stearate, PEG-100 stearate, PEG-120 stearate, and PEG-150 stearate. Preferred for use in the compositions herein is PEG-100 stearate.

Preferably, ethylene glycol ethers of fatty alcohols as described in the above (3) or (8) are used as the nonionic surfactants in the composition of the present invention.

Ethylene glycol ethers of fatty alcohols useful herein include any ethylene glycol ethers of fatty alcohols which are suitable for use in a hair conditioning composition. No limiting examples of the ethylene glycol ethers of fatty alcohols include; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 100, which are ethylene glycol ethers of steareth alcohol, wherein the numeric designation indicates the number of ethylene glycol moieties present; ceteareth 1 through ceteareth-50, which are the ethylene glycol ethers of ceteareth alcohol, i.e. a mixture of fatty alcohols containing predominantly cetyl and stearyl alcohol, wherein the numeric designation indicates the number of ethylene glycol moieties present; polyoxyethylene ethers of branched alcohols such as octyldodecyl alochol, dodecylpentadecyl alcohol, hexyldecyl alcohol, and isostearyl alcohol; and mixtures thereof. Preferred for use herein is ceteareth-20.

UV Absorber

The compositions of the present invention may contain a UV (ultraviolet) absorber. UV absorbers are particularly useful for compositions of the present invention which are substantially transparent. The UV absorbers herein are preferably used at levels by weight of the composition of from about 0.01% to about 10%.

UV absorbers useful herein can be water soluble or water insoluble, including: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, -phenyl cinnamonitrile; butyl cinnamoyl pyruvate; trihydroxycinnamic acid derivatives (esculetin, methylesculetin, daphnetin, and the glucosides, esculin and daphnin); dibenzalacetone and benzalacetophenone; naphtholsulfonates (sodium salts of 2-naphthol-3,6-disulfonic and of 2-naphthol-6,8-disulfonic acids); dihydroxynaphthoic acid and its sals; o- and p-Hydroxybiphenyidisulfonates; quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbityl) (6-propyl piperonyl) ether; hydroquinone; benzophenones (oxybenzene, sulisobenzone, dioxybenzone, benzoresorcinol, 2,2",4,4'-Tetrahydroxybenzophenone, 2,2'-Dihydroxy-4,4'-dimethoxybenzophenone, octabenzone); 4-Isopropyidibenzoylmethane; butylmethoxydibenzoylmethane; etocrylene; and 4-isopropyl-di-benzoylmethane. Of these, 2-ethylhexyl p-methoxycinnamate, 4,4'-t-butyl methoxydibenzoylmethane, 2-hydroxy-4-methoxybenzophenone, octyidimethyl p-aminobenzoic acid, digalloyltrioleate, 2,2-dihydroxy-4-methoxybenzophenone ethyl 4-[bis(hydroxypropyl)] aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylamino-benzoate, 2-phenylbenzimidazole-5-sulfonic acid, 2-(p-dimethylaminophenyl)-5-sulfonicbenzoxazoic acid and mixtures thereof. Preferred sunscreens useful in the compositions of the present invention are 2-ethylhexyl p-methoxycinnamate, butylmethoxydibenzoylmethane, 2-hydroxy-4-methoxybenzophenone, octyldimethyl p-aminobenzoic acid and mixtures thereof.

High Molecular Weight Ester Oils

High molecular weight ester oils are useful herein. The high molecular weight ester oils useful herein are those which are water insoluble, have a molecular weight of at least about 500, preferably at least about 800, and are in liquid form at 25° C. Useful high molecular weight ester oils herein include trimethylol ester oils, poly α-olefin oils, citrate ester oils, glyceryl ester oils, and mixtures thereof. As used herein, the term "water insoluble" means the compound is substantially not soluble in water at 25° C.; when the compound is mixed with water at a concentration by weight of above 1.0%, preferably at above 0.5%, the compound is temporarily dispersed to form an unstable colloid in water, then is quickly separated from water into two phases.

The high molecular weight ester oil herein provides conditioning benefits such as moisturized feel, smooth feel, and manageability control to the hair when the hair is dried, yet does not leave the hair feeling greasy. It is believed that water insoluble oily material in general are capable of being deposited on the hair. Without being bound by theory, it is believed that, because of its bulkiness, the high molecular weight ester oil covers the surface of the hair and, as a result, the high molecular weight ester oil reduces hair friction to deliver smoothness and manageability control to the hair. It is also believed that, because it has some hydrophilic groups, the high molecular weight ester oil provides moisturized feel, yet, because it is liquid, does not leave the hair feeling greasy. The high molecular weight ester oil is chemically stable under normal use and storage conditions.

Trimethylol ester oils useful herein are those having the following formula:

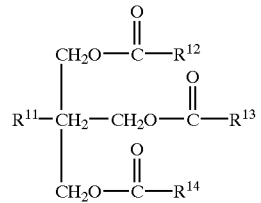

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons. Preferably, $R^{11}$ is ethyl and $R^{12}$, $R^{13}$, and $R^{14}$, independently, are branched, straight, saturated, or unsaturated alkyl groups having from 8 to about 22 carbons. More preferably, $R^{11}$, $R^{12}$, $R^{13}$ and $R^{14}$ are defined so that the molecular weight of the compound is from about 800 to about 1200.

Poly α-olefin oils useful herein are those having the following formula and having a viscosity of from about 1 to about 35,000 cst, a molecular weight of from about 200 to about 60,000, and a polydispersity of no more than about 3;

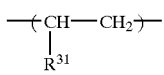

wherein $R^{31}$ is an alkyl having from about 4 to 14 carbons, preferably 4 to 10 carbons. Poly α-olefin oils having a molecular weight of at least about 800 are useful herein. Such high molecular weight poly α-olefin oils are believed to provide long lasting moisturized feel to the hair. Poly α-olefin oils having a molecular weight of less than about 800 are useful herein. Such low molecular weight poly α-olefin oils are believed to provide a smooth, light, clean feel to the hair.

Citrate ester oils useful herein are those having a molecular weight of at least about 500 having the following formula:

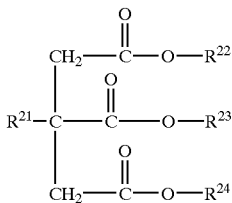

wherein $R^{21}$ is OH or $CH_3COO$, and $R^{22}$, $R^{23}$, and $R^{24}$, independently, are branched, straight, saturated, or unsaturated alkyl, aryl, and alkylaryl groups having from 1 to about 30 carbons. Preferably, $R^{21}$ is OH, and $R^{22}$, $R^{23}$, and $R^{24}$, independently, are branched, straight, saturated, or unsaturated alkyl, aryl, and alkylaryl groups having from 8 to about 22 carbons. More preferably, $R^{21}$, $R^{22}$, $R^{23}$ and $R^{24}$ are defined so that the molecular weight of the compound is at least about 800.

Glyceryl ester oils useful herein are those having a molecular weight of at least about 500 and having the following formula:

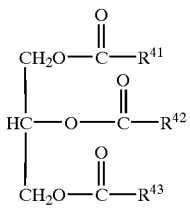

wherein $R^{41}$, $R^{42}$, and $R^{43}$, independently, are branched, straight, saturated, or unsaturated alkyl, aryl, and alkylaryl groups having from 1 to about 30 carbons.

Preferably, $R^{41}$, $R^{22}$, and $R^{23}$, independently, are branched, straight, saturated, or unsaturated alkyl, aryl, and alkylaryl groups having from 8 to about 22 carbons. More preferably, $R^{41}$, $R^{42}$, and $R^{43}$ are defined so that the molecular weight of the compound is at least about 800.

Particularly useful trimethylol ester oils herein include trimethylolpropane triisostearate, trimethylolpropane trioleate, and mixtures thereof. Such compounds are available from Shin-nihon Rika with tradenames PTO, ENUJERUBU TP3SO.

Particularly useful poly α-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Mobil Chemical Co.

Particularly useful citrate ester oils herein include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Additional Oily Compounds

Additional oily compounds useful herein include fatty alcohols and their derivatives, fatty acids and their derivatives, and hydrocarbons. The additional oily compounds useful herein may be volatile or nonvolatile, and have a melting point of not more than about 25° C. Without being bound by theory, it is believed that, the additional oily compounds may penetrate into the hair to modify the hydroxy bonds of the hair, thereby resulting in providing softness and flexibility to the hair. The additional oily compounds of this section are to be distinguished from the high melting point compounds described above. Nonlimiting examples of the additional oily compounds are found in International Cosmetic Ingredient Dictionary, Fifth Edition, 1993, and CTFA Cosmetic Ingredient Handbook, Second Edition, 1992.

The fatty alcohols useful herein include those having from about 10 to about 30 carbon atoms, preferably from about 12 to about 22 carbon atoms, and more preferably from about 16 to about 22 carbon atoms. These fatty alcohols can be straight or branched chain alcohols and can be saturated or unsaturated alcohols, preferably unsaturated alcohols. Nonlimiting examples of these compounds include oleyl alcohol, palmitoleic alcohol, isostearyl alcohol, isocetyl alchol, undecanol, octyl dodecanol, octyl decanol, octyl alcohol, caprylic alcohol, decyl alcohol and lauryl alcohol.

The fatty acids useful herein include those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Suitable fatty acids include, for example, oleic acid, linoleic acid, isostearic acid, linolenic acid, ethyl linolenic acid, ethyl linolenic acid, arachidonic acid, and ricinolic acid.

The fatty acid derivatives and fatty alcohol derivatives are defined herein to include, for example, esters of fatty alcohols, alkoxylated fatty alcohols, alkyl ethers of fatty alcohols, alkyl ethers of alkoxylated fatty alcohols, and bulky ester oils such as pentaerythritol ester oils, trimethylol ester oils, citrate ester oils, glyceryl ester oils, and mixtures thereof. Nonlimiting examples of fatty acid derivatives and fatty alcohol derivatives, include, for example, methyl linoleate, ethyl linoleate, isopropyl linoleate, isodecyl oleate, isopropyl oleate, ethyl oleate, octyidodecyl oleate, oleyl oleate, decyl oleate, butyl oleate, methyl oleate, octyldodecyl stearate, octyldodecyl isostearate, octyldodecyl isopalmitate, octyl isopelargonate, octyl pelargonate, hexyl isostearate, isopropyl isostearate, isodecyl isononanoate, isopropyl stearate, ethyl stearate, methyl stearate and Oleth-2. Bulky ester oils such as pentaerythritol ester oils, trimethylol ester oils, citrate ester oils and glyceryl ester oils useful herein are those which have a molecular weight of less than about 800, preferably less than about 500.

The hydrocarbons useful herein include straight chain, cyclic, and branched chain hydrocarbons which can be either saturated or unsaturated, so long as they have a melting point of not more than about 25° C. These hydrocarbons have from about 12 to about 40 carbon atoms, preferably from about 12 to about 30 carbon atoms, and preferably from about 12 to about 22 carbon atoms. Also encompassed herein are polymeric hydrocarbons of alkenyl monomers, such as polymers of $C_{2-6}$ alkenyl monomers. These polymers can be straight or branched chain polymers. The straight chain polymers will typically be relatively short in length, having a total number of carbon atoms as described above. The branched chain polymers can have substantially higher chain lengths. The number average molecular weight of such materials can vary widely, but will typically be up to about 500, preferably from about 200 to about 400, and more preferably from about 300 to about 350. Also useful herein are the various grades of mineral oils. Mineral oils are liquid mixtures of hydrocarbons that are obtained from petroleum. Specific examples of suitable hydrocarbon materials include paraffin oil, mineral oil, dodecane, isododecane, hexadecane, isohexadecane, eicosene, isoeicosene, tridecane, tetradecane, polybutene, polyisobutene, and mixtures thereof. Preferred for use herein are hydrocarbons selected from the group consisting of mineral oil, poly α-olefin oils such as isododecane, isohexadecane, polybutene, polyisobutene, and mixtures thereof.

Commercially available fatty alcohols and their derivatives useful herein include: oleyl alcohol with tradename UNJECOL 90BHR available from Shin Nihon Rika, various liquid esters with tradenames SCHERCEMOL series available from Scher, and hexyl isostearate with a tradename HIS and isopropryl isostearate having a tradename ZPIS available from Kokyu Alcohol. Commercially available bulky ester oils useful herein include: trimethylolpropane tricaprylate/tricaprate with tradename MOBIL ESTER P43 from Mobil Chemical Co. Commercially available hydrocarbons useful herein include isododecane, isohexadecane, and isoeicosene with tradenames PERMETHYL 99A, PERMETHYL 101A, and PERMETHYL 1082, available from Presperse (South Plainfield N.J., USA), a copolymer of isobutene and normal butene with tradenames INDOPOL H-100 available from Amoco Chemicals (Chicago Ill., and USA), mineral oil with tradename BENOL available from Witco, isoparaffin with tradename ISOPAR from Exxon Chemical Co. (Houston Tex., USA.)

Other Additional Components

The compositions of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as glutamic acid, citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate, antidandruff agents such as zinc pyrithione; and mixtures thereof.

Product Forms

The hair conditioning compositions of the present invention can be in the form of rinse-off products or leave-on products, can be transparent or opaque, and can be formulated in a wide variety of product forms, including but not limited to creams, gels, emulsions, mousses and sprays. Preferably, the compositions of the present invention are in the form of leave-on products.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

All percentages herein are based upon the total weight of the compositions of the present invention, unless otherwise specified. All such weight percentages as they pertain to listed ingredients are based on the active level and, therefore, do not include carriers or by-products that may be included in commercially available materials.

Compositions (wt %)

|  | Ex. 1 | Ex. 2 | Ex. 3 | Ex. 4 | Ex. 5 | Ex. 6 |
|---|---|---|---|---|---|---|
| Cyclomethicone/Dimethicone *1 | 96.0 | — | 91.69 | 92.69 | — | 80.0 |
| Cyclomethicone/Dimethiconol *2 | — | 96.0 | — | — | 83.69 | 7.69 |
| Isoparaffin *3 | — | — | — | — | 10.0 | — |
| PEG modified glyceride *4 | 4.0 | — | 8.0 | 1.0 | — | 12.0 |
| PEG modified glyceryl fatty acid ester *5 | — | 4.0 | — | — | 1.0 | — |
| Dimethicone copolyol-1 *6 | — | — | — | 4.0 | — | — |
| Dimethicone copolyol-2 *7 | — | — | — | — | 1.0 | — |
| Polypropylene Glycol-1 *8 | — | — | — | 1.0 | — | — |
| Polypropylene Glycol-2 *9 | — | — | — | — | 4.0 | — |

-continued

| Compositions (wt %) | | | | | | |
|---|---|---|---|---|---|---|
| Pentaerythritol Tetraisostearate *10 | — | — | — | 1.0 | — | — |
| Vitamin E *11 | — | — | 0.01 | 0.01 | 0.01 | 0.01 |
| Panthenol *12 | — | — | 0.05 | 0.05 | 0.05 | 0.05 |
| Panthenyl ethyl ether *13 | — | — | 0.05 | 0.05 | 0.05 | 0.05 |
| Benzophenone-3 *14 | — | — | 0.05 | 0.05 | 0.05 | 0.05 |
| Octyl Methoxycinnamate *15 | — | — | 0.05 | 0.05 | 0.05 | 0.05 |
| Perfume solution | — | — | 0.1 | 0.1 | 0.1 | 0.1 |

| | Ex. 7 | Ex. 8 | Ex. 9 | Ex. 10 | Ex. 11 | Ex. 12 |
|---|---|---|---|---|---|---|
| Cyclomethicone/Dimethicone *1 | 45.5 | — | 23.0 | 50.0 | 60.0 | 40.0 |
| Cyclomethicone/Dimethiconol *2 | — | 45.5 | — | — | — | 5.5 |
| Isoparaffin *3 | — | — | — | — | — | 10.0 |
| PEG modified glyceride *4 | 4.0 | 8.0 | 4.0 | 4.0 | 4.0 | — |
| PEG modified glyceryl fatty acid ester *5 | — | — | — | — | 4.0 | 2.0 |
| Dimethicone copolyol-1 *6 | — | — | 4.0 | — | — | — |
| Dimethicone copolyol-2 *7 | — | — | — | — | — | 1.0 |
| Polypropylene Glycol-1 *8 | — | — | — | 4.0 | — | — |
| Polypropylene Glycol-2 *9 | — | — | — | — | — | 1.0 |
| Pentaerythritol Tetraisostearate *10 | — | — | — | — | 4.0 | — |
| Acrylates/C10–30 Alkyl acrylate crosspolymer *16 | 0.2 | 0.2 | 0.1 | 0.4 | — | — |
| Carbomer *17 | — | — | 0.1 | 0.1 | — | |
| Cetyl hydroxyethyl cellulose *18 | — | — | — | — | 0.2 | 0.2 |
| Polyquaternium-39 *19 | 2.0 | — | 4.0 | 1.0 | — | — |
| Polyquaternium-22 *20 | — | 2.0 | — | — | — | — |
| Polyethylene Glycol 200 *21 | 2.0 | 2.0 | 1.0 | 4.0 | — | — |
| Cetrimonium chloride *22 | — | — | — | — | 2.0 | — |
| Stearamidopropyl dimethylamine *23 | — | — | — | — | — | 1.6 |
| λ-Glutamic acid *24 | — | — | — | — | — | 0.5 |
| Polyquaternium-10 *25 | — | — | — | — | 0.4 | 0.4 |
| Cetyl Alcohol *26 | — | — | — | — | 1.3 | 1.3 |
| Stearyl Alcohol *27 | — | — | — | — | 0.8 | 0.8 |
| PEG-60 Hydrogenated castor oil *28 | — | — | — | — | 0.2 | 0.2 |
| Ethanol | — | — | 10.0 | — | — | — |
| Vitamin E *11 | 0.01 | 0.01 | 0.01 | 0.01 | 0.01 | 0.01 |
| Hydrolyzed collagen *29 | 0.01 | 0.01 | 0.01 | 0.01 | 0.01 | 0.01 |
| Panthenol *12 | 0.05 | 0.05 | 0.05 | 0.05 | 0.05 | 0.05 |
| Panthenyl ethyl ether *13 | 0.05 | 0.05 | 0.05 | 0.05 | 0.05 | 0.05 |
| Benzophenone-3 *14 | 0.05 | 0.05 | 0.05 | 0.05 | 0.05 | 0.05 |
| Octyl Methoxycinnamate *15 | 0.05 | 0.05 | 0.05 | 0.05 | 0.05 | 0.05 |
| Methyl Paraben | 0.2 | 0.2 | 0.2 | 0.2 | 0.2 | 0.2 |
| Phenoxyethanol | 0.3 | 0.3 | 0.3 | 0.3 | 0.3 | 0.3 |
| Triethanolamine | 0.2 | 0.2 | 0.2 | 0.5 | — | — |
| Disodium EDTA | 0.13 | 0.13 | 0.1 | 0.1 | 0.1 | 0.1 |
| Perfume solution | 0.05 | 0.05 | 0.1 | 0.1 | 0.1 | 0.1 |
| Deionized Water | q.s. to 100% | | | | | |

| | Ex. 13 | Ex. 14 | Ex. 15 |
|---|---|---|---|
| Cyclomethicone/Dimethicone *30 | 96.0 | 92.69 | 80.0 |
| Cyclomethicone/Dimethiconol *2 | — | — | 2.69 |
| Isoparaffin *3 | — | — | 5.0 |
| PEG modified glyceride *4 | 4.0 | 1.0 | — |
| PEG modified glyceryl fatty acid ester *5 | — | — | 6.0 |
| Dimethicone copolyol-1 *6 | — | 4.0 | — |
| Dimethicone copolyol-2 *7 | — | — | 4.0 |
| Polypropylene Glycol-1 *8 | — | 1.0 | — |
| Polypropylene Glycol-2 *9 | — | — | 1.0 |
| Pentaerythritol Tetraisostearate *10 | — | 1.0 | 1.0 |
| Vitamin E *11 | — | 0.01 | 0.01 |
| Panthenol *12 | — | 0.05 | 0.05 |
| Panthenyl ethyl ether *13 | — | 0.05 | 0.05 |
| Benzophenone-3 *14 | — | 0.05 | 0.05 |
| Octyl Methoxycinnamate *15 | — | 0.05 | 0.05 |
| Perfume solution | — | 0.1 | 0.1 |

| | Ex. 16 | Ex. 17 | Ex. 18 |
|---|---|---|---|
| Cyclomethicone/Dimethicone *30 | 45.5 | 30.0 | 40.0 |
| Cyclomethicone/Dimethiconol *2 | — | — | 5.5 |
| Isoparaffin *3 | — | — | 10.0 |
| PEG modified glyceride *4 | 4.0 | 4.0 | — |
| PEG modified glyceryl fatty acid ester *5 | — | 4.0 | 2.0 |

-continued

| Compositions (wt %) | | | |
|---|---|---|---|
| Dimethicone copolyol-1 *6 | — | 1.0 | — |
| Dimethicone copolyol-2 *7 | — | — | 1.0 |
| Polypropylene Glycol-1 *8 | — | 1.0 | — |
| Polypropylene Glycol-2 *9 | — | — | 1.0 |
| Pentaerythritol Tetraisostearate *10 | — | 4.0 | — |
| Acrylates/C10–30 Alkyl acrylate crosspolymer *16 | 0.2 | 0.2 | — |
| Carbomer *17 | — | 0.1 | — |
| Cetyl hydroxyethyl cellulose *18 | — | — | 0.2 |
| Polyquaternium-39 *19 | 2.0 | — | — |
| Polyquaternium-22 *20 | — | 2.0 | — |
| Polyethylene Glycol 200 *21 | 2.0 | 2.0 | — |
| Cetrimonium chloride *22 | — | — | 1.0 |
| Stearamidopropyl dimethylamine *23 | — | — | 1.6 |
| λ Glutamic acid *24 | — | — | 0.5 |
| Polyquaternium-10 *25 | — | 0.4 | 0.4 |
| Cetyl Alcohol *26 | — | 1.3 | 1.3 |
| Stearyl Alcohol *27 | — | 0.8 | 0.8 |
| PEG-60 Hydrogenated castor oil *28 | — | 0.2 | 0.2 |
| Ethanol | — | — | — |
| Vitamin E *11 | 0.01 | 0.01 | 0.01 |
| Hydrolyzed collagen *29 | 0.01 | 0.01 | 0.01 |
| Panthenol *12 | 0.05 | 0.05 | 0.05 |
| Panthenyl ethyl ether *13 | 0.05 | 0.05 | 0.05 |
| Benzophenone-3 *14 | 0.05 | 0.05 | 0.05 |
| Octyl Methoxycinnamate *15 | 0.05 | 0.05 | 0.05 |
| Methyl Paraben | 0.2 | 0.2 | 0.2 |
| Phenoxyethanol | 0.3 | 0.3 | 0.3 |
| Triethanolamine | 0.2 | — | — |
| Disodium EDTA | 0.13 | 0.1 | 0.1 |
| Perfume solution | 0.05 | 0.1 | 0.1 |
| Deionized Water | q.s. to 100% | | |

| | Ex. 19 | Ex. 20 |
|---|---|---|
| Cyclomethicone/Dimethicone *30 | 45.5 | 30.0 |
| PEG modified glyceride *4 | 4.0 | 4.0 |
| PEG modified glyceryl fatty acid ester *5 | — | 4.0 |
| Dimethicone copolyol-1 *6 | — | 1.0 |
| Polypropylene Glycol-1 *8 | — | 1.0 |
| Pentaerythritol Tetraisostearate *10 | — | 4.0 |
| Acrylates/C10–30 Alkyl acrylate crosspolymer *16 | 0.2 | 0.2 |
| Carbomer *17 | — | 0.1 |
| Polyquaternium-39 *19 | 2.0 | — |
| Polyquaternium-22 *20 | — | 2.0 |
| Polyethylene Glycol 200 *21 | 2.0 | 2.0 |
| Polyquaternium-10 *25 | — | 0.4 |
| Cetyl Alcohol *26 | — | 1.3 |
| Stearyl Alcohol *27 | — | 0.8 |
| PEG-60 Hydrogenated castor oil *28 | — | 0.2 |
| PVP/VA copolymer *31 | 2.0 | 2.0 |
| Vitamin E *11 | 0.01 | 0.01 |
| Hydrolyzed collagen *29 | 0.01 | 0.01 |
| Panthenol *12 | 0.05 | 0.05 |
| Panthenyl ethyl ether *13 | 0.05 | 0.05 |
| Benzophenone-3 *14 | 0.05 | 0.05 |
| Octyl Methoxycinnamate *15 | 0.05 | 0.05 |
| Methyl Paraben | 0.2 | 0.2 |
| Phenoxyethanol | 0.3 | 0.3 |
| Triethanolamine | 0.2 | — |
| Disodium EDTA | 0.13 | 0.1 |
| Perfume solution | 0.05 | 0.1 |
| Deionized Water | q.s. to 100% | |

Definitions of Components
*1 Cyclomethicone/Dimethicone Mixture of 15% of Dimethicone Gum and 85% of Cyclomethicone, wherein the Dimethicone gum has a molecular weight of from about 400,000 to about 600,000 and viscosity of from about 4,000,000 to about 20,000,000 mPa · s, and Cyclomethicone is decamethylcyclopentasiloxane) available from General Electric
*2 Cyclomethicone/Dimethiconol: DCQ2-1401 (Mixture of 13% of Dimethiconol and 87% of Cyclomethicone, wherein the Dimethiconol has a molecular weight of from about 400,000 to about 600,000 and viscosity of from about 4,000,000 to about 20,000,000 mPa · s, and Cyclomethicone is decamethylcyclopentasiloxane) available from Dow Corning
*3 Isoparaffin: Isopar C (C7-8 Isoparaffin) available from Exxon
*4 PEG modified glyceride: Tagat TO available from Goldschmidt Chemical -continued Compositions (wt %)

*5 PEG modified glyceryl fatty acid ester: Tagat S available from Goldschmidt Chemical
*6 Dimethicone copolyol-1: Abil B 8830 available from Goldschmidt Chemical
*7 Dimethicone copolyol-2: Abil B 8852 available from Goldschmidt Chemical
*8 Polypropylene glycol-1: New Pol PP-2000 available from Sanyo Kasei
*9 Polypropylene glycol-2: New Pol PP-4000 available from Sanyo Kasei
*10 Pentaerythritol Tetraisostearate: KAKPTI available from Koukyu Alcohol Kogyo
*11 Vitamin E: Emix-d Available from Eisai
*12 Panthenol: Available from Roche
*13 Panthenyl ethyl ether: Available from Roche
*14 Benzophenone-4: Uvnul MS-40 available from BASF
*15 Octyl Methoxycinnamate: Parasol MCX available from Roche
*16 Acrylates/C10–30 Alkyl acrylate crosspolymer: Pemulen TR1 available from BF Goodrich
*17 Carbomer: Carbopol 981 available from BF Goodrich
*18 Cetyl Hydroxyethyl cellulose: Natrosol Plus CS Grade 330 available from Aqualon
*19 Polyquaternium-39: Merquat Plus 3330 available from Calgon
*20 Polyquaternium-22: Merquat 280 available from Calgon
*21 Polyethylene Glycol: Carbowax PEG-200 available from Union Carbide
*22 Cetrimonium chloride: Varisoft CTB40 available from Witco Chemicals
*23 Stearamidopropyl dimethylamine: available from Inolex
*24 λ-Glutamic acid: Available from Ajinomoto
*25 Polyquaternium-10: Ucare KG30M available from Amerchol
*26 Cetyl Alcohol: Konol series available from Shinnihon Rika
*27 Stearyl Alcohol: Konol series available from Shinnihon Rika
*28 PEG-60 Hydrogenated castor oil: Cremophor PH-60 available from BASF
*29 Hydrolyzed collagen: Peptein 2000 available from Hormel
*30 Cyclomethicone/Dimethicone: Mixture of 25% of Dimethicone Gum and 75% of Cyclomethicone, wherein the Dimethicone gum has a molecular weight of from about 150,000 to about 200,000 and viscosity of about 1,000,000 mPa · s, and Cyclomethicone is decamethylcyclopentasiloxane, available from General Electric
*31 PVP/VA copolymer: Luviskol 73W available from BASF Method of Preparation The polymeric materials such as the thickening agents, amphoteric conditioning polymers, and cationic conditioning polymers, if present, are dispersed in water at room temperature, and mixed by vigorous agitation. The frizz control agents and additional frizz control agents, if present, are added to the mixture, and mixed by vigorous agitation until fully dispersed. The non-volatile silicone compound and volatile compound are also added to the mixture, and mixed by vigorous agitation until fully dispersed. Neutralizing agent is added, if anionic polymers present, for neutralization. The high melting point compounds and cationic surfactants, if included, are added to the mixture with agitation at above 70° C. by either melting such components or by dissolving such components. Then the mixture is cooled to below 30° C., and then the remaining components such as styling polymers, if included, are added to the mixture with agitation.

Examples 1 through 12 are hair conditioning compositions of the present invention which are particularly useful for leave-on use. These examples have many advantages. For example, they can provide improved conditioning benefits to the hair, especially provide improved frizz control benefit in addition to other conditioning benefits such as smoothness, softness, and reduction of friction, and leave the hair and hands with a clean feeling.

Examples 13 through 18 are also hair conditioning compositions of the present invention which are particularly useful for leave-on use. These examples have many advantages. For example, they can provide improved conditioning benefits to the hair, especially provide improved frizz control benefit in addition to other conditioning benefits such as smoothness, softness, and reduction of friction, and leave the hair and hands with a clean feeling.

Examples 19 and 20 are also hair conditioning compositions of the present invention which are particularly useful for leave-on use. These examples have many advantages. For example, they can provide well-balanced conditioning and styling benefits, i.e., can provide styling benefits such as hair style achievement, and hold and retention, while delivering improved conditioning benefits such as frizz control benefit, smoothness, softness, and reduction of friction while reducing sticky and greasy feeling.

It is understood that the examples and embodiments described herein are for illustrative purposes only and that various modifications or changes in light thereof will be suggested to one skilled in the art without departing from its spirit and scope.

What is claimed is:

1. A hair conditioning composition comprising:
    (1) a non-volatile silicone compound having a viscosity of from about 500,000 to about 50,000,000 mPa.s said non-volatile silicone being selected from the group consisting of silicone gums, polyaryl siloxanes, polyalkyl siloxanes, polyalkylaryl siloxanes, silicone resins, and alkylamino substituted silicones;
    (2) a volatile compound selected from the group consisting of an isoparaffin hydrocarbon having a boiling point of from about 60 to about 260° C., a volatile silicone compound from 2 to 7 silicon atoms, and mixtures thereof; and
    (3) a frizz control agent which is a PEG-modified glycerides having the structure:

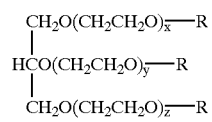

wherein one or more of the R groups is selected from saturated or unsaturated fatty acid moieties derived from animal or vegetable oils wherein the fatty acid moieties have a carbon length chain of from 12 and 22, any other R groups are hydrogen, x, y, z are independently zero or more, the average sum of x+y+z is equal to from about 10 to about 45.

2. The hair conditioning composition according to claim 1 wherein the sum of x+y+z is equal to from about 20 to 30.

3. The hair conditioning composition according to claim 1 wherein the non-volatile silicone compound is Dimethicone or Dimethiconol.

4. The hair conditioning composition according to claim 1 wherein the volatile compound is a volatile cyclic silicone compound having the formula:

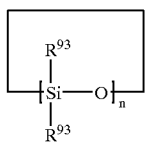

wherein $R^{93}$ is independently alkyl or aryl, and n is an integer of from 3 to 7.

5. The hair conditioning composition according to claim 1 further comprising an additional frizz control agent selected from the group consisting of (i), (ii), (iii), (iv), and (v):

(i) dimethicone copolyols having the structure:

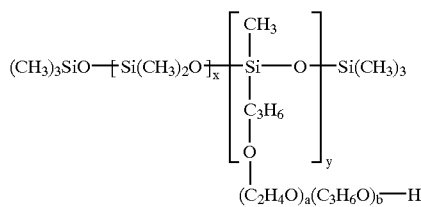

wherein x is an integer from 1 to 2000, y is an integer from 1 to 1000, a is zero or greater, b is zero or greater, the sum of a+b is at least 1, and having an HLB value of about 20 or less;

(ii) dimethicone copolyols having the structure:

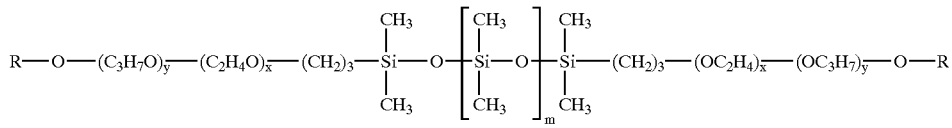

wherein R is selected from the group consisting of hydrogen, methyl, and combinations thereof, m is an integer from 1 to 2000, x is independently zero or greater, y is independently zero or greater, wherein the dimethicone copolyol has at least one ethylene oxide and/or propylene oxide, and has an HRB value of about 20 or less;

(iii) polypropylene glycol having a weight average molecular weight of from about 200 g/mol to about 100,000 g/mol; and (iv) pentacrythritol ester oils having the formula:

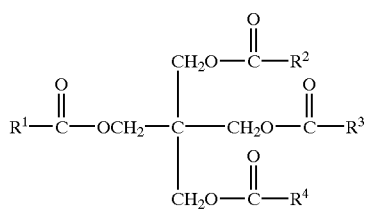

wherein $R^1$, $R^2$, $R^3$, and $R^4$, independently, are branched, straight, saturated, or unsaturated alkyl, aryl, and alkylaryl groups from 1 to about 30 carbons; and (v) mixtures thereof.

6. The hair conditioning composition according to claim 1, wherein the composition is a leave-on composition.

7. The hair conditioning composition according to claim 1, wherein the composition is non-aqueous and comprises by weight:
 (1) from about 1% to about 30% of the non-volatile silicone compound;
 (2) from about 50% to about 98.9% of the volatile compound; and
 (3) from about 0.1% to about 20% of the fizz control agent.

8. The hair conditioning composition according to claim 1, wherein the composition is aqueous and comprises by weight:
 (1) from about 0.5% to about 20% of the non-volatile silicone compound;
 (2) from about 5% to about 70% of the volatile compound;
 (3) from about 0.1% to about 20% of the frizz control agent;
 (4) from about 0.01% to about 10% of a thickening agent; and
 (5) an aqueous carrier.

9. The hair conditioning composition according to claim 8 wherein the thickening agent is selected from the group consisting of a carboxylic acid/carboxylate copolymer, a hydrophobically modified cellulose ether, and mixtures thereof.

10. The hair conditioning composition according to claim 9 wherein the thickening agent is a carboxylic acid/carboxylate copolymer.

11. The hair conditioning composition according to claim 10 wherein the carboxylic acid/carboxylate copolymer is an acrylic acid/alkyl acrylate copolymer having the following formula:

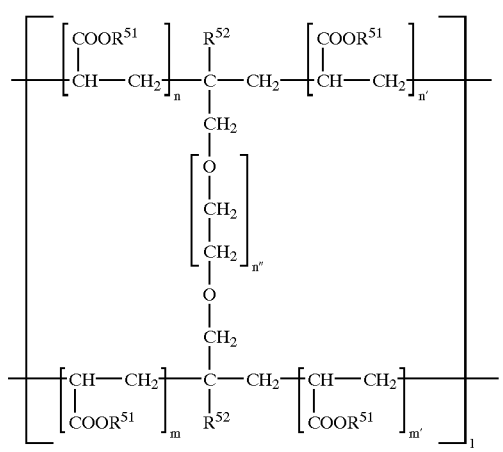

wherein $R^{51}$, independently, is a hydrogen or an alkyl of 1 to 30 carbons wherein at least one of $R^{51}$ is a hydrogen, $R^{52}$ is a hydrogen or an alkyl group from about 1 to about 30, n, n', m and m' are integers in which n+n'+m+m' is from about 40 to about 100, n" is an integer of from 1 to about 30, and l is defined so that the copolymer has a weight average molecular weight of about 500,000 to about 3,000,000.

12. The hair conditioning composition according to claim 8 further comprising an amphoteric conditioning polymer.

13. The hair conditioning composition according to claim 8 further comprising a humectant.

14. The hair conditioning composition according to claim 8 further comprising a water-soluble styling polymer.

15. The hair conditioning composition according to claim 14, wherein the water-soluble styling polymer comprises vinylpyrrolidone copolymer.

16. The hair conditioning composition according to claim 15, wherein the vinylpyrrolidone copolymer is a polypyrrolidone/vinyl acetate copolymer.

* * * * *

UNITED STATES PATENT AND TRADEMARK OFFICE
CERTIFICATE OF CORRECTION

PATENT NO. : 6,709,648 B2
DATED : March 23, 2004
INVENTOR(S) : T. Sako et al.

It is certified that error appears in the above-identified patent and that said Letters Patent is hereby corrected as shown below:

<u>Column 43,</u>
Line 45, "HRB" should read -- HLB --.
Line 50, "pentacrythritol" should read -- pentaerythritol --.

<u>Column 44,</u>
Line 8, "fizz" should read -- frizz --.

Signed and Sealed this

Fifth Day of April, 2005

JON W. DUDAS
*Director of the United States Patent and Trademark Office*